US010052212B2

(12) United States Patent
Fiechter et al.

(10) Patent No.: US 10,052,212 B2
(45) Date of Patent: Aug. 21, 2018

(54) INTERVERTEBRAL IMPLANT WITH IMPROVED FASTENING SYSTEM FOR THE FIXING PLATE

(71) Applicant: MEDACTA INTERNATIONAL SA, Castel San Pietro (CH)

(72) Inventors: Meinrad Fiechter, Lugano (CH); Francesco Siccardi, Vico Morcote (CH); Marco Riva, Longone al Segrino (IT)

(73) Assignee: MEDACTA INTERNATIONAL SA, Castel San Pietro (CH)

(*) Notice: Subject to any disclaimer, the term of this patent is extended or adjusted under 35 U.S.C. 154(b) by 0 days.

(21) Appl. No.: 13/767,202

(22) Filed: Feb. 14, 2013

(65) Prior Publication Data
US 2013/0218276 A1    Aug. 22, 2013

(30) Foreign Application Priority Data

Feb. 17, 2012   (EP) .................................... 12155953

(51) Int. Cl.
*A61F 2/44*   (2006.01)
*A61F 2/30*   (2006.01)
(Continued)

(52) U.S. Cl.
CPC .......... *A61F 2/4455* (2013.01); *A61F 2/4465* (2013.01); *A61B 17/7059* (2013.01);
(Continued)

(58) Field of Classification Search
CPC .......... A61F 2/4455; A61F 2002/30392; A61F 2002/30393; A61F 2002/304;
(Continued)

(56) References Cited

U.S. PATENT DOCUMENTS 5,683,394 A * 11/1997 Rinner ................. A61F 2/4455
606/247
6,156,037 A * 12/2000 LeHuec et al. ............... 606/247
(Continued)

FOREIGN PATENT DOCUMENTS

CN        1053004 A      7/1991
CN      101068513 A     11/2007
(Continued)

OTHER PUBLICATIONS

European Search Report / EP 12 15 5953 completed Aug. 3, 2012 in Berlin.

*Primary Examiner* — Eric S Gibson
*Assistant Examiner* — Marcela I Shirsat
(74) *Attorney, Agent, or Firm* — Allen, Dyer, Doppelt + Gilchrist, P.A.

(57) ABSTRACT

An Intervertebral implant (100) for the fusion between two vertebral bodies of a vertebral column comprising: an internally hollow fusion cage (1); a fixing plate (2); and cooperating features (8, 10, 17, 19, 20, 21) for fastening said fixing plate (2) on the anterior side of the fusion cage (1); the cooperating features (8, 10, 17, 19, 20, 21) comprising restraining means (8, 17) meant to restrain the fixing plate (2) in a posterior-anterior direction with respect to the fusion cage (1) and pivoting means (10, 19) being arranged to guide a rotation, about a pivot axis (x), of said fixing plate (2) with respect to said fusion cage (1).

23 Claims, 4 Drawing Sheets (51) Int. Cl.
  *A61B 17/70* (2006.01)
  *A61F 2/28* (2006.01)
(52) U.S. Cl.
  CPC .......... *A61F 2/30965* (2013.01); *A61F 2/442* (2013.01); *A61F 2002/2835* (2013.01); *A61F 2002/304* (2013.01); *A61F 2002/3008* (2013.01); *A61F 2002/30364* (2013.01); *A61F 2002/30365* (2013.01); *A61F 2002/30367* (2013.01); *A61F 2002/30383* (2013.01); *A61F 2002/30387* (2013.01); *A61F 2002/30388* (2013.01); *A61F 2002/30393* (2013.01); *A61F 2002/30395* (2013.01); *A61F 2002/30401* (2013.01); *A61F 2002/30426* (2013.01); *A61F 2002/30492* (2013.01); *A61F 2002/30507* (2013.01); *A61F 2002/30509* (2013.01); *A61F 2002/30517* (2013.01); *A61F 2002/30578* (2013.01); *A61F 2002/30604* (2013.01); *A61F 2002/30607* (2013.01); *A61F 2002/30616* (2013.01); *A61F 2002/30774* (2013.01); *A61F 2002/30777* (2013.01); *A61F 2002/30787* (2013.01); *A61F 2002/30789* (2013.01); *A61F 2002/30792* (2013.01); *A61F 2002/30794* (2013.01); *A61F 2002/30841* (2013.01); *A61F 2002/30843* (2013.01); *A61F 2002/4475* (2013.01); *A61F 2310/00023* (2013.01); *A61F 2310/00796* (2013.01)

(58) Field of Classification Search
  CPC .... A61F 2002/30403; A61F 2002/2835; A61F 2002/30364; A61F 2002/30367; A61F 2002/30387; A61F 2002/30388; A61F 2002/30383; A61F 2002/30395; A61F 2002/30401; A61F 2002/30365
  USPC ............. 623/17.11–17.16; 606/900, 901, 99, 606/86 A, 70–71, 280–299, 247
  See application file for complete search history.

(56) References Cited

U.S. PATENT DOCUMENTS

| | | | | |
|---|---|---|---|---|
| 6,235,059 | B1 * | 5/2001 | Benezech et al. | 623/17.16 |
| 6,648,715 | B2 * | 11/2003 | Wiens et al. | 446/121 |
| 6,699,288 | B2 | 3/2004 | Moret | |
| 7,112,222 | B2 * | 9/2006 | Fraser et al. | 623/17.11 |
| 7,172,627 | B2 * | 2/2007 | Fiere et al. | 623/17.11 |
| 7,621,938 | B2 | 11/2009 | Molz, IV | |
| 7,740,662 | B2 * | 6/2010 | Barnett et al. | 623/20.33 |
| 8,025,684 | B2 | 9/2011 | Garcia-Bengochea et al. | |
| 8,100,975 | B2 | 1/2012 | Waugh et al. | |
| 8,328,872 | B2 | 12/2012 | Duffield et al. | |
| 8,480,747 | B2 | 7/2013 | Melkent et al. | |
| 2004/0193269 | A1 | 9/2004 | Fraser et al. | |
| 2006/0085071 | A1 * | 4/2006 | Lechmann | A61B 17/86 623/17.11 |
| 2008/0161925 | A1 | 7/2008 | Brittan et al. | |
| 2008/0300634 | A1 * | 12/2008 | Gray | A61B 17/7059 606/280 |
| 2009/0005874 | A1 | 1/2009 | Fleischmann et al. | |
| 2009/0210064 | A1 * | 8/2009 | Lechmann et al. | 623/17.16 |
| 2010/0030334 | A1 * | 2/2010 | Molz, IV | 623/17.11 |
| 2010/0312346 | A1 * | 12/2010 | Kueenzi | A61F 2/44 623/17.16 |
| 2011/0040382 | A1 | 2/2011 | Muhanna | |
| 2012/0109313 | A1 | 5/2012 | Mathieu et al. | |
| 2012/0143336 | A1 | 6/2012 | Aflatoon et al. | |
| 2013/0053894 | A1 | 2/2013 | Gamache et al. | |
| 2013/0060337 | A1 | 3/2013 | Petersheim et al. | |
| 2013/0238095 | A1 | 9/2013 | Pavento et al. | |
| 2013/0310937 | A1 * | 11/2013 | Pimenta | A61F 2/4425 623/17.15 |
| 2013/0345814 | A1 | 12/2013 | Walkenhorst et al. | |
| 2014/0107786 | A1 | 4/2014 | Geisler et al. | |
| 2014/0194994 | A1 | 7/2014 | Duffield et al. | |
| 2014/0214166 | A1 | 7/2014 | Theofilos | |
| 2015/0320571 | A1 | 11/2015 | Lechmann et al. | |

FOREIGN PATENT DOCUMENTS

| | | | |
|---|---|---|---|
| CN | 102038563 | A | 5/2011 |
| EP | 0079695 | A2 | 5/1983 |
| EP | 1103236 | A2 | 5/2001 |
| EP | 1834608 | A2 | 9/2007 |
| EP | 2628466 | | 8/2013 |
| EP | 2628467 | | 8/2013 |
| FR | 2 747 034 | | 10/1997 |
| GB | 2457673 | A * | 8/2009 |
| JP | 2012501744 | A | 1/2012 |
| WO | 20040069106 | | 8/2004 |
| WO | 2007065993 | | 6/2007 |
| WO | 2008102174 | A2 | 8/2008 |
| WO | 2010107692 | A1 | 9/2010 |
| WO | 2013134210 | | 12/2013 |

* cited by examiner

INTERVERTEBRAL IMPLANT WITH IMPROVED FASTENING SYSTEM FOR THE FIXING PLATE

CROSS-REFERENCE TO RELATED APPLICATIONS

This application claims priority to European Patent Application No. 12155953.8, filed Feb. 17, 2012, which is hereby incorporated herein by reference in its entirety.

FIELD OF THE INVENTION

The present invention relates to the general field of orthopedic surgical implants.

In particular, the invention relates to an intervertebral implant permitting the fusion between two vertebral bodies of a vertebral column, used in the field of surgical spine treatment.

More specifically, the implant is preferably intended to be used as stand-alone intervertebral body fusion device for Anterior Lumbar Interbody Fusion (ALIF).

PRIOR ART

The ALIF approach is a surgical technique mainly used to operate a damaged disk in the lumbar area of the spine. The operation involves approaching the spine through an incision in the abdomen, removing the damaged disk and substituting it with a suitable intervertebral implant.

The intervertebral implant mainly comprises a hollow cage, which is inserted between the two vertebral bodies and filled with autogenic bone graft or the like in order to promote bone growth and eventual fusion of the two bodies.

Moreover, the implant comprises a fixing plate solidly attached to the hollow cage. The fixing plate may or may not protrude out of the intervertebral space and is fixed to the anterior sides of the two adjacent vertebral bodies, usually by means of two or more bone screws. The main function of the fixing plate and screws is that of improving primal stability of the whole implant.

It should be noted that the fixing plate is preferably formed as a separate piece and subsequently mounted on the anterior side of the fusion cage.

Such a design solution provides two different advantages.

Firstly, such a design gives the opportunity of manufacturing the fusion cage and the fixing plate out of different materials: usually the cage, which is required to be radiolucent, is made out of PEEK material, while the plate is made out of titanium.

Secondly, thanks to the two-pieces design the implant may be assembled by the surgeon right before the operation. In such a way, the fixing plate may be conveniently selected out of a set of different plates adapted to different surgical requirements.

It should be stressed that, in implants of the above kind, the role of the fastening system used for mounting the fixing plate on the fusion cage is critical, since its design derives from a trade-off between a plurality of conflicting needs.

Firstly, the fastening system should be easily operated, so that the surgeon may mount the final implant without wasting unnecessary time or energy. Possibly, the final mounting should be possible even when the fusion cage has been already positioned between the intervertebral space of the patient.

Secondly, the fastening system should be integrated within the dimensions of a standard intervertebral implant. In this respect, cumbersome designs should be avoided and the system should be kept as simple as possible.

Thirdly, the fastening system should provide an adequate primal stability to the implant. The fixing plate should be solidly attached to the fusion cage and the risk of a post-operational slip or disengagement should be minimized.

Several systems have been proposed in the prior art to mount the fixing plate on the fusion cage, based for instance on mortise and tenon or button-like fasteners. Those known systems are disclosed for instance in the following European patents and patent applications: EP 0 79 695, EP 0 891 169, EP 1 103 236, EP 1 476 098 and EP 1 589 909. Nonetheless, all of these system present drawbacks with respect to one or more of the above-listed requirements.

In view of the foregoing, the technical problem underlying the present invention is to provide an intervertebral implant with a two-pieces design whereas the system for fastening the fixing plate on the fusion cage overcomes the drawbacks of the prior art solutions.

SUMMARY OF THE INVENTION

The abovementioned technical problem is solved by an intervertebral implant for the fusion between two vertebral bodies of a vertebral column comprising:
  a fusion cage, extending from a posterior side to an anterior side, adapted to be interposed between two adjacent vertebral bodies of a patient;
  a fixing plate having at least one passageway, for instance for receiving a bone screw;
wherein the fusion cage and the fixing plate comprise cooperating features for fastening the fixing plate on the anterior side of the fusion cage; in particular, the cooperating features comprise restraining means and pivoting means, the pivoting means being arranged to guide a rotation, about a pivot axis, of said fixing plate with respect to said fusion cage, said rotation bringing the implant from a first configuration, in which the fixing plate is freely displaceable in a posterior-anterior direction with respect to the fusion cage, to a second configuration in which the displacement of the fixing plate in a posterior-anterior direction with respect to the fusion cage is restrained by the restraining means.

The restraining means may advantageously comprise at least one protruding portion, radially extending with respect to said pivot axis, and at least one recessed portion intended to house said protruding portion in the second configuration of the implant.

The cooperating feature may advantageously comprise a bulging head and a housing cavity for housing said bulging head, the protruding portion being provided on a lateral edge of the bulging head, the recessed portion being provided on a lateral edge of the housing cavity.

Advantageously, two protruding portions may be provided on the two opposite lateral edges of the bulging head, two recessed portions being provided on the two opposite lateral edges of the housing cavity.

The bulging head may advantageously be integral with the fixing plate, the housing cavity being provided on the fusion cage.

The bulging head may be rotatably coupled to the housing cavity by means of the pivoting means, said pivoting means comprising a centering pin rotatably inserted in a corresponding centering hole.

The centering pin may project from the bulging head, the centering hole being provided on the bottom of the housing cavity. Obviously, an alternative and opposite construction may be provided with the centering pin projecting from the housing cavity and the centering hole formed in the bulging head.

The recessed portion may advantageously define a slideway in which the protruding portion slidably engages during rotation of the fixing plate from the first to the second configuration.

The recessed portion and the protruding portion may be dovetailed in cross section.

The slideway defined by the recessed portion may comprise an abutment intended to block the rotation of the fixing plate with respect to the fusion cage upon reaching the second configuration.

The profile of the recessed portion and the profile of the protruding portion may comprise local features designed to cooperate in order to determine a snap fit of the fixing plate upon reaching the second configuration.

The above-mentioned local features may comprise a locking recess on the profile of the recessed portion and a locking protrusion on the profile of the protruding portion.

The fusion cage may be conveniently made out of radiolucent material, for instance PEEK.

The fixing plate may be conveniently made of a material different from that of the fusion cage, for instance titanium.

The fixing plate may be advantageously selected among a plurality of fixing plates having different geometries.

Further features and advantages of the intervertebral implant according to the invention shall be made clearer by the description, given herein below, of a specific embodiment described by way of non-limiting example with reference to the accompanying drawings.

DETAILED DESCRIPTION

Referring to FIGS. 1-5, with 100 is globally shown an intervertebral implant according to present invention.

Figures 6, 7, 8, 13:
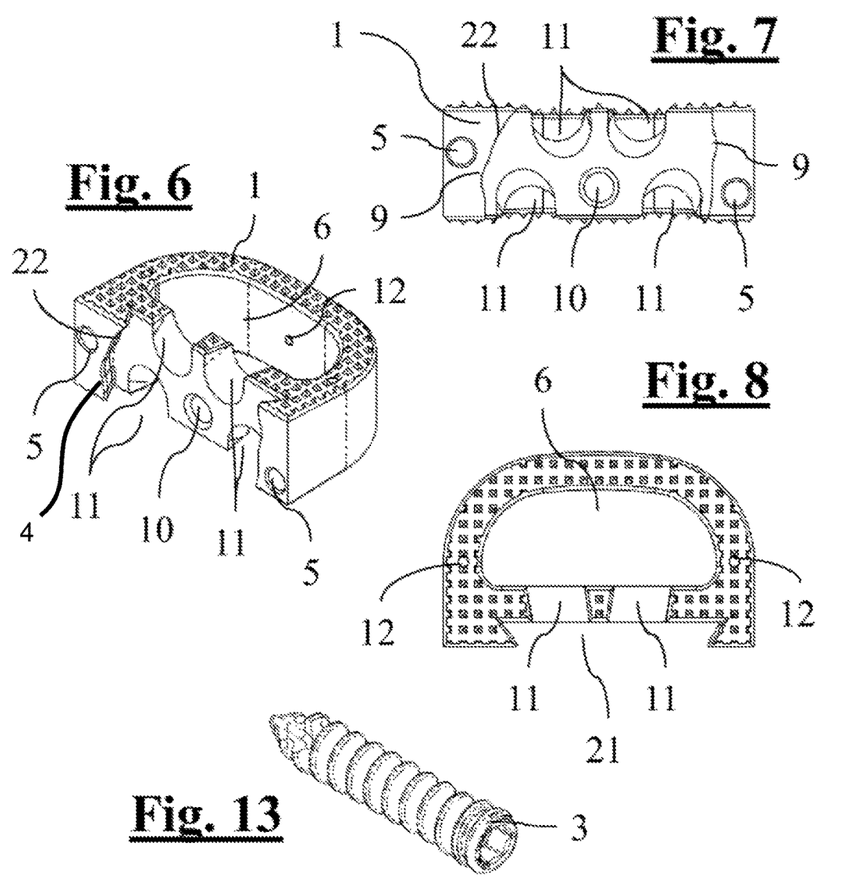
FIG. 6 shows a perspective view of a fusion cage being part of the intervertebral implant.
FIG. 7 shows an anterior view of the fusion cage.
FIG. 8 shows a top view of the fusion cage.
FIG. 13 shows a perspective view of a bone screw being part of the intervertebral implant.
Figure 12:
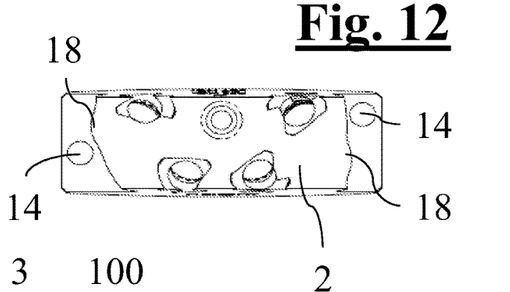
FIG. 12 shows a posterior view of the fixing plate in FIG. 9.

The intervertebral implant 100 comprises a fusion cage 1, depicted alone in FIGS. 6-8, coupled to a fixing plate 2, depicted alone in FIG. 12, by means of a fastening system which form the main object of the present invention.

Figure 14:
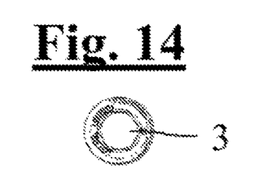
FIG. 14 shows an anterior view of the bone screw.
Figure 15:
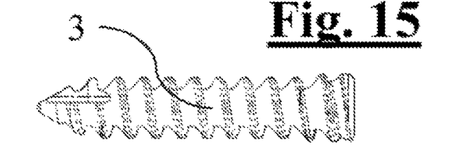
FIG. 15 shows a side view of the bone screw.

The intervertebral implant 100 may further comprise four bone screws 3, one of which is depicted in FIGS. 13-15.

The fusion cage 1, intended to be inserted within the intervertebral space of a patient, features four walls of uniform height raising from a substantially rectangular base and enclosing a central hole 6.

The posterior side of the fusion cage 1, which is the side inserted between the vertebral bodies, exhibit rounded edges, while the anterior side, which has to be coupled with the fixing plate 2, has straight edges.

The central hole 6, extending in caudal-cranial direction, is intended to be filled with material for bone growth promotion, such as autogenic bone graft. The caudal and cranial cage surface are advantageously covered by a toothed pattern in order to improve primal stability.

The anterior side of the fusion cage 1 exhibits a housing cavity 21, roughly rectangular in size, extending along the whole height of the fusion cage. The structure and function of the housing cavity 21 will be further discussed into detail in connection to the fixing plate 2.

The anterior side of the fusion cage 1 further exhibits two anti-rotation blind holes 5, opening at different heights on the two side portions of the anterior surface bordering the housing cavity 21. The scope of this holes is just for a use by a removable installation instrument.

The anterior wall of the fusion cage 1 exhibits four apertures 11 opening on the bottom of the housing cavity 21 and reaching the central hole 6. Two of them apertures 11 open on the caudal surface, while the other two open on the cranial surface of the cage. Such apertures 11 are provided to allow the passage of bone screws 3 the head of which is blocked on the fixing plate 2, as illustrated, for example, in FIGS. 3 and 4. As the skilled in this art may appreciate, the apertures 11 may host alternative kind of screws such as locking screws, poly-axial screws or compression screws, in this last case even a relating security mechanism would be provided.

The bottom surface of the housing cavity further exhibits a centering hole 10, the function of which will be readily apparent from the following description.

The fusion cage 1 is made out of biocompatible material, for instance PEEK, CFRP or titanium, with or without a coating, for example a titanium or hydroxyapatite coating could be provided even if other coating may be used. Three radiopaque markers 12 are embedded in the PEEK structure in order to control the exact positioning of the implant with X-Rays; two of the markers 12 cross the lateral walls of the fusion cage in a caudal-cranial direction, while the third marker 12 crosses the posterior wall following an anterior-posterior direction.

A first, preferred embodiment of the fixing plate 2 has a substantially rectangular planar structure, the perimeter of which matches that of the anterior side of the fusion cage 1. In particular, the height of the plate 2 matches the height of the fusion cage 1.

Figure 9:
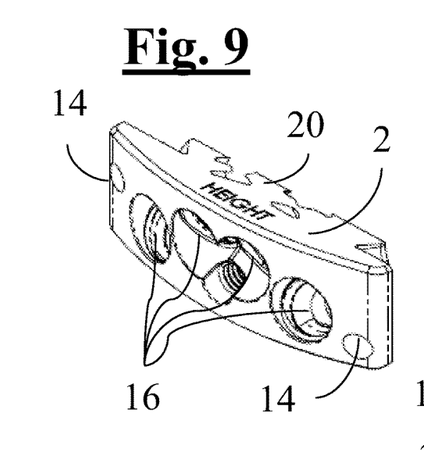
FIG. 9 shows a perspective view of a fixing plate being part of the intervertebral implant.
Figure 10:
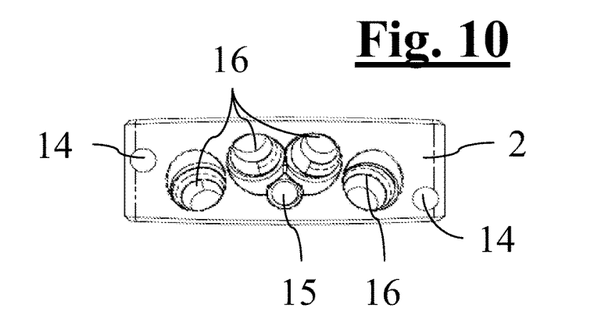
FIG. 10 shows an anterior view of the fixing plate in FIG. 9.
Figure 11:
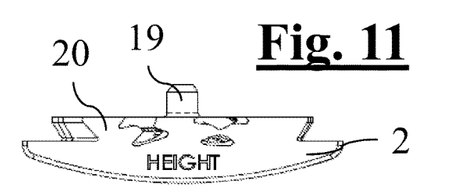
FIG. 11 shows a top view of the fixing plate in FIG. 9.

The fixing plate 2 exhibits four passageways 16 running from its anterior to its posterior side.

The passageways 16 are symmetrically arranged in couples; two central passageways are inclined upwards (i.e. towards the cranial direction), the other two lateral passageways are inclined downwards (i.e. towards the caudal direction).

Figure 1:
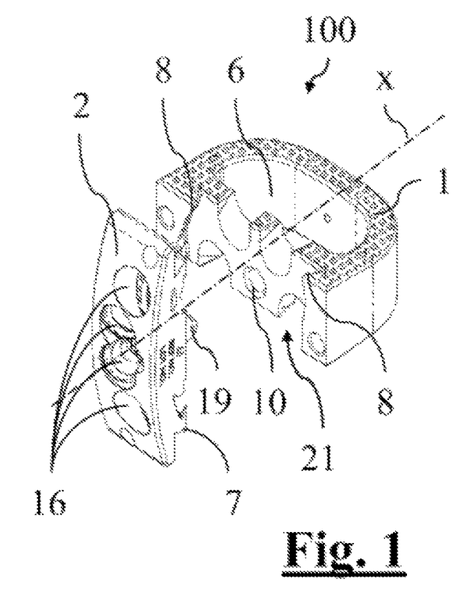
FIG. 1 shows a perspective view of an intervertebral implant according to the invention, its fixing plate and fusion cage being detached.
Figure 2:
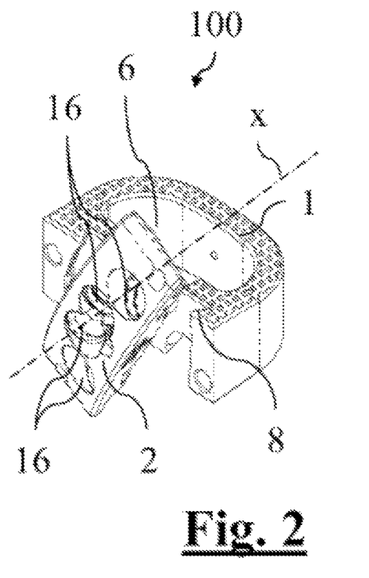
FIG. 2 shows a perspective view of the intervertebral implant in a first configuration.
Figure 3:
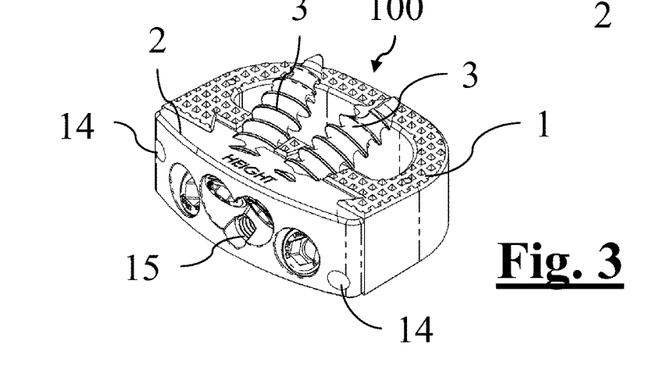
FIG. 3 shows a perspective view of the intervertebral implant in a second configuration.
Figures 4, 5:
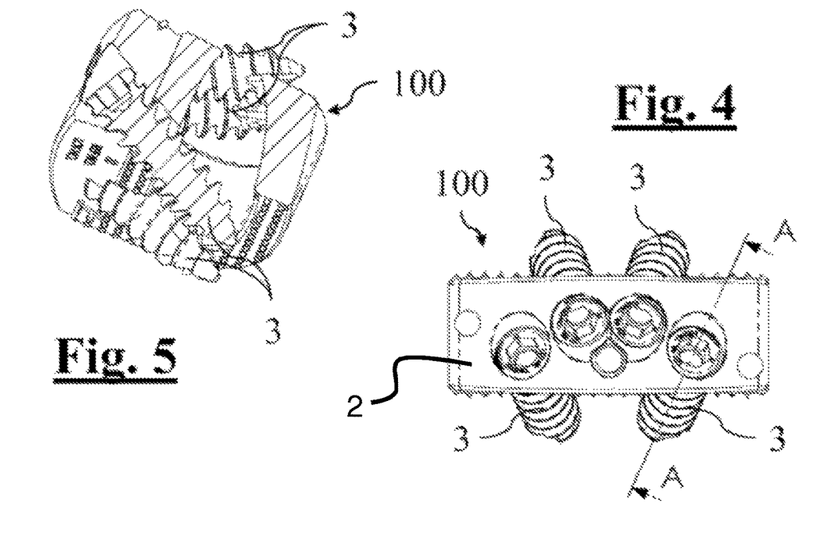
FIG. 4 shows an anterior view of the intervertebral implant in the second configuration.
FIG. 5 shows a cross sectional view of the intervertebral implant taken along the cutting plane "A-A" identified in FIG. 4.

When the fixing plate 2 is correctly attached to the fusion cage 1, the apertures 11 are aligned with the passageways 16 and may be traversed for instance by the bone screws 3.

On its anterior side, the fixing plate 2 has a central threaded hole 15 which is placed slightly below the opening of the two central passageways 16. The threaded hole 15 serves the purpose of temporarily coupling the fixing plate 2 with a surgical instrument for placing the implant during the surgical operation.

The fixing plate 2 also features anti-rotation through bores 14. The anti-rotation through bores 14, opening laterally with respect to the lateral passageways 16, cross the plate from side to side and align with the anti-rotation blind holes 5 of the fusion cage 1 when the fixing plate 2 is correctly mounted hereon.

On its posterior side, the fixing plate 2 has a bulging head 20 protruding in posterior direction. The bulging head 20 is meant to be housed within the housing cavity of the fusion cage 1, and therefore has a similar rectangular shape. The height of the bulging head 20 equals the height of the fusion cage 1. Since in the embodiment herein described the fixing plate 2 also shares the same height with the fusion cage 1, the posterior side of the fixing plate 2 only has two lateral planes aside from the bulging head 20.

A centering pin 19 orthogonally extends from the posterior surface of the bulging head 20; such a centering pin 19 is meant to be inserted in the centering hole 10 realized on the fusion cage 1. Obviously, an alternative and opposite construction may be provided with the centering pin 19 projecting from the fusion cage and the centering hole 10 formed in the bulging head 20.

The pin inserted in the hole determines a pivot axis x, lying on the sagittal mid-plane of the fusion cage 1, toward the caudal side. In other words, the pin 19 and the hole 10 may be considered a fast on or a bayonet coupling.

The two lateral edges of the bulging head 20 present a protruding portion 7, extending radially with respect to the pivot axis x. The two protruding portions 7 have a dovetailed cross section, which is tapered toward the posterior direction.

On the other hand, the two opposite lateral edges of the housing cavity 21 feature a recessed portion 8, which is counter-shaped with respect to the corresponding protruding portion 7 and adapted to house it.

Moving further into detail, it should be noted that the recessed portion 8 define a slideway into which the corresponding protruding portion 7 enters when the bulging head 20 is rotated about the pivot axis x with respect to the housing cavity 21.

From the description above, one can clearly understand how the fixing plate 2 is blocked on the fusion cage 1.

Firstly, the fixing plate 2 being kept inclined with respect to the fusion cage 1, the centering pin 19 is inserted within the centering hole 10. Such a configuration, depicted in FIG. 2, will be referred herein as first configuration.

Secondly, the fixing plate 2 is rotated about the pivot axis x determined by the centering pin 19 and hole 10. During the rotation, the protruding portions 7 of the bulging head 20 slidably engage in the slideway defined by the recessed portion 8 of the housing cavity 21.

The rotation is carried on upon reaching a second configuration, depicted for instance in FIG. 4, wherein the fixing plate 2 is aligned with the fusion cage 1.

The second configuration is the operative configuration of the device; only when the implant 100 is in its second configuration the bone screw 3 may be introduced into the appropriate passageways 16.

It should be noted that, in order to allow the slidable engagement between the protruding portions 7 and the recessed portions 8, the profile of said portions should at least partially follow that of a circumference centered in the pivot axis x.

However, one of the recessed portions 8 has a profile end 4 deviating from said circumference in order to define an abutment 22. The profile of the corresponding protruding portions 7 is of course counter-shaped and deviates in a similar way.

The abutment 22 is intended to first guide and then to stop or block the rotation of the fixing plate with respect to the fusion cage upon reaching the second configuration. The profile of this abutment is carefully designed in order to implement both the above mentioned function of guiding and stopping.

Moreover, both the protruding portions 7 locally feature a locking protrusion 18 along their profile, while the recessed portions 8 similarly feature a counter-shaped locking recess 9.

The locking protrusions 18 and recesses 9 are designed to cooperate with each other in order to determine a snap fit of the fixing plate 2 upon reaching the second configuration.

The fixing plate 2 is conveniently realized with a biocompatible metal, for instance PEEK, CFRP, titanium or with another alternative material suitable for implantable medical devices.

Figures 9A, 9B, 9C:
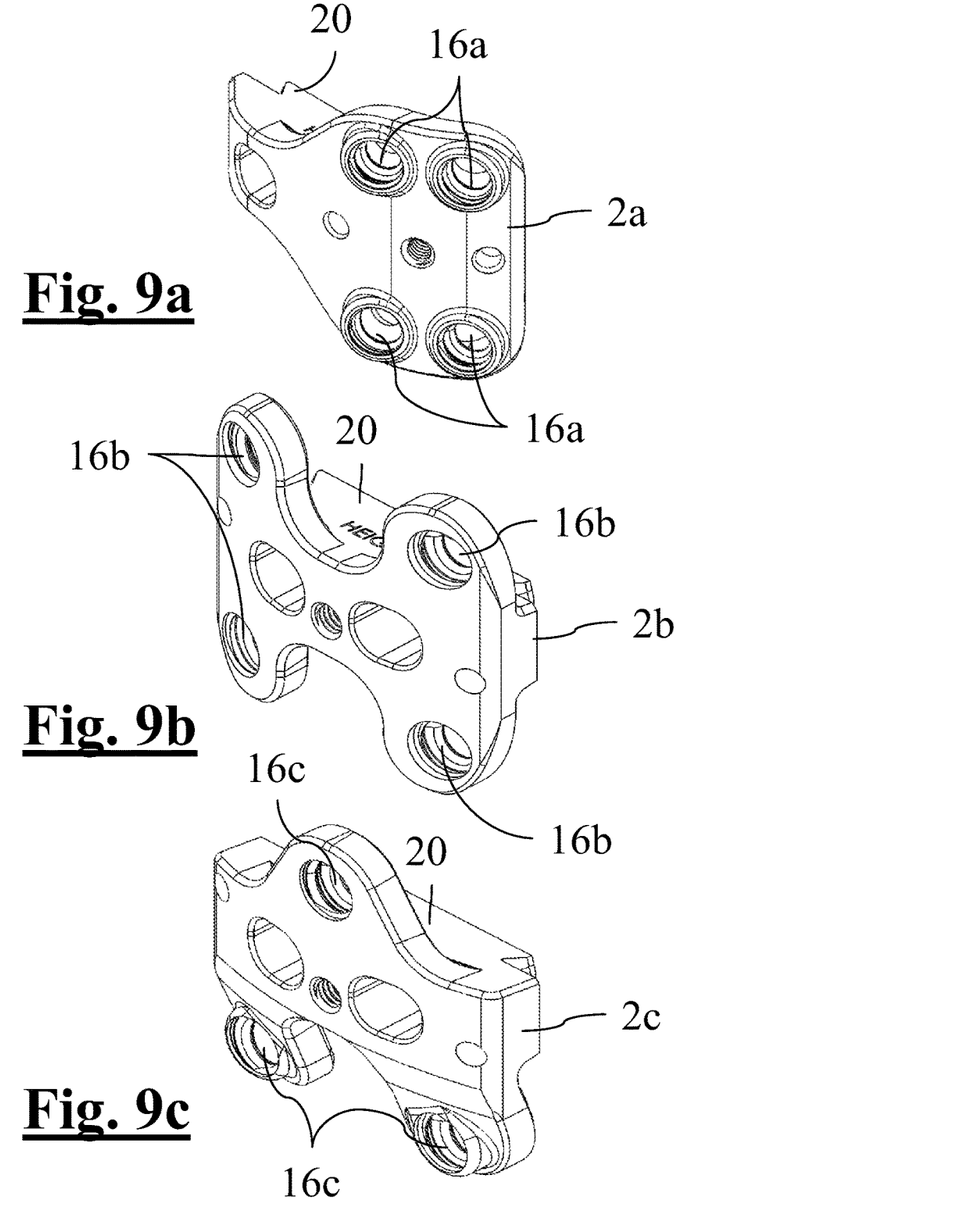
FIG. 9a shows a perspective view of a second embodiment, alternative to the one in FIG. 9, of a fixing plate being part of the intervertebral implant.
FIG. 9b shows a perspective view of a third embodiment of a fixing plate being part of the intervertebral implant.
FIG. 9c shows a perspective view of a fourth embodiment of a fixing plate being part of the intervertebral implant.

Instead of the fixing plate 2 described above, the surgeon may select a an alternative fixing plate 2a, 2b, 2c adapted to the specific need of the operation.

In FIGS. 9a-9c, some alternative plates embodiments are depicted which extend beyond the height of the fusion cage 1 in both caudal and cranial direction.

In a second embodiment, the fixing plate 2a has four passageways 16a all arranged on the same side of the device, so that all screw may be inserted from this side therefore reducing the size of the surgical incision needed. An alternative configuration with only two passageways 16a may be used as well.

In a third embodiment, the fixing plate 2b has four lobes featuring the passageways 16b. The device is intended for increased stability of the implant.

In a fourth embodiment, the fixing plate 2c has an upper lobe and two lower lobes, each of them featuring a passageway 16c. Such a device is specifically designed for fusing together the vertebrae L5 and S1.

It should be noted that all alternative embodiments for the fixing plate 2a, 2b, 2c feature a bulging head 20 of the above-described type, allowing them to be coupled to the same fusion cage. In particular, alternative kind of screws may be used such as locking screws, poly-axial screws or even compression screws together with their relating security mechanisms.

Obviously a person skilled in the art, in order to meet specific needs, will readily acknowledge the possibility of changes and variations to the intervertebral implant described above, all comprised within the scope of protection defined by the following claims.

For instance, even if the preferred embodiment previously described is designed to be used as stand-alone intervertebral body fusion device for Anterior Lumbar Interbody Fusion, a person skilled in the art will readily acknowledge that the same solution can be used for different kind of intervertebral implants, for instance: anterior cervical intervertebral body fusion devices, extreme lateral intervertebral body fusion devices, or posterior intervertebral body fusion devices. The number of screws employed will obvious change in respect to the approach/implant design: in an extreme lateral cage and in a cervical cage two screws are more favorable than four screws. The implant geometry will also change in respect to the approach.

The invention claimed is:

1. An intervertebral implant for fusion between adjacent vertebral bodies of a vertebral column, the intervertebral implant comprising:
 a fusion cage interposable between the adjacent vertebral bodies, the fusion cage comprising first and second opposing sidewalls, a first anterior side between the first and second opposing sidewalls, and a first posterior side opposite the first anterior side between the first and second opposing sidewalls and defining a passageway between the first posterior and first anterior sides,
 the first anterior side comprising a peripheral portion defining an asymmetric wedge-shaped abutment, and a medial portion being recessed with respect to the peripheral portion and defining an alignment passageway for a pivot axis; and
 a fixing plate comprising
  a second anterior side,
  a second posterior side being wedge-shaped and opposing the second anterior side, the second posterior side configured to engage with the medial portion, and
  a centering pin extending from the second posterior side and configured to be inserted into the alignment passageway to align the fusion cage and the fixing plate along the pivot axis and to allow the fixing plate to rotate about the pivot axis with respect to the fusion cage, the second posterior side configured to engage with the asymmetric wedge-shaped abutment to limit rotation of the fixing plate in a single direction.

2. The intervertebral implant according to claim 1, wherein said second anterior side is integral with said second posterior side.

3. The intervertebral implant according to claim 1, wherein the centering pin extends from a bottom of the second posterior side; and wherein the alignment passageway is at a bottom of the first anterior side.

4. The intervertebral implant according to claim 1, wherein the medial portion defines a slideway in which the second posterior side slidably engages during rotation of the fixing plate.

5. The intervertebral implant according to claim 1, wherein the medial portion and the second posterior side are dovetailed in cross-section.

6. The intervertebral implant according to claim 1, wherein a profile of the medial portion and a profile of the second posterior side comprise interlocking features configured to provide a snap fit of the fixing plate upon reaching a locked configuration.

7. The intervertebral implant according to claim 6, wherein the interlocking features comprise a locking recess on the profile of the medial portion and a locking protrusion on the profile of the second posterior side.

8. The intervertebral implant according to claim 1, wherein the fusion cage comprises a first biocompatible material.

9. The intervertebral implant according to claim 8, wherein the fixing plate comprises a second biocompatible material different from the first biocompatible material.

10. The intervertebral implant according to claim 1, further comprising a biocompatible metal layer at least partially coating at least one of said fusion cage and said fixing plate.

11. The intervertebral implant according to claim 10, wherein the biocompatible metal layer comprises at least one of titanium and hydroxyapatite.

12. The intervertebral implant according to claim 1, wherein the fixing plate is selected from among a plurality of fixing plates having different geometries.

13. The intervertebral implant according to claim 1, wherein the fixing plate defines at least one passageway configured to receive at least one bone screw.

14. The intervertebral implant according to claim 13, wherein said at least one passageway is configured to host a plurality of different screw types.

15. The intervertebral implant according to claim 14, wherein the plurality of different screw types comprises locking screws, poly-axial screws, compression screws, and combinations thereof.

16. The intervertebral implant according to claim 1, wherein in a locked configuration, the fixing plate is locked to the first anterior side of the fusion cage after a rotation of the fixing plate.

17. An intervertebral implant for fusion between adjacent vertebral bodies of a vertebral column, the intervertebral implant comprising:
 a fusion cage interposable between the adjacent vertebral bodies, the fusion cage comprising first and second opposing sidewalls, a first anterior side between the first and second opposing sidewalls, and a first posterior side opposite the first anterior side between the first and second opposing sidewalls and defining a passageway between the first posterior and first anterior sides,
 the first anterior side comprising a peripheral portion defining an asymmetric wedge-shaped abutment, and a medial portion being recessed with respect to the peripheral portion and defining an alignment passageway for a pivot axis;
 a fixing plate comprising
  a second anterior side,
  a second posterior side being integral with said second anterior side and being wedge-shaped and opposing the second anterior side, the second posterior side configured to engage with the medial portion, and
  a centering pin extending from the second posterior side and configured to be inserted into the alignment passageway to align the fusion cage and the fixing plate along the pivot axis and to allow the fixing plate to rotate about the pivot axis with respect to the fusion cage, the second posterior side configured to engage with the asymmetric wedge-shaped abutment to limit rotation of the fixing plate in a single direction; and
 a biocompatible metal layer at least partially coating at least one of said fusion cage and said fixing plate.

18. The intervertebral implant according to claim 17, wherein the medial portion defines a slideway in which the second posterior side slidably engages during rotation of the fixing plate.

19. The intervertebral implant according to claim 17, wherein a profile of the medial portion and a profile of the second posterior side comprise interlocking features configured to provide a snap fit of the fixing plate upon reaching a locked configuration.

20. The intervertebral implant according to claim 17, wherein the fusion cage comprises a first biocompatible material.

21. The intervertebral implant according to claim 20, wherein the fixing plate comprises a second biocompatible material different from the first biocompatible material.

22. The intervertebral implant according to claim 17, wherein the fixing plate defines at least one passageway configured to receive at least one bone screw.

23. The intervertebral implant according to claim 17, wherein the biocompatible metal layer comprises at least one of titanium and hydroxyapatite.

* * * * *